US006368268B1

(12) United States Patent
Sandvick et al.

(10) Patent No.: US 6,368,268 B1
(45) Date of Patent: Apr. 9, 2002

(54) METHOD AND DEVICE FOR INTERACTIVE VIRTUAL CONTROL OF SEXUAL AIDS USING DIGITAL COMPUTER NETWORKS

(76) Inventors: Warren J. Sandvick, 7015 61st St., Lubbock, TX (US) 79407; Jim W. Hughes, 1619 Kingsway, Oak Grove, MO (US) 64075; David Alan Atkinson, 1205 Valley View La., Joplin, MO (US) 64804

( * ) Notice: Subject to any disclaimer, the term of this patent is extended or adjusted under 35 U.S.C. 154(b) by 0 days.

(21) Appl. No.: 09/134,751

(22) Filed: Aug. 17, 1998

(51) Int. Cl.[7] .................................................. A61F 5/00
(52) U.S. Cl. ........................................................ 600/38
(58) Field of Search ...................... 600/38; 128/897–98

(56) References Cited

U.S. PATENT DOCUMENTS

| | | | |
|---|---|---|---|
| 3,874,373 | A | 4/1975 | Sobel |
| 3,978,851 | A | 9/1976 | Sobel |
| 4,412,535 | A | 11/1983 | Teren |
| 4,790,296 | A | 12/1988 | Segal |
| 4,834,115 | A | 5/1989 | Stewart |
| 5,063,915 | A | 11/1991 | Wyckoff |
| 5,437,605 | A | 8/1995 | Helmy |
| 5,454,840 | A | 10/1995 | Krakovsky et al. |
| 5,462,051 | A | 10/1995 | Oka et al. |
| 5,467,773 | A | 11/1995 | Bergelson et al. |
| 5,490,784 | A | 2/1996 | Carmein |
| 5,501,650 | A | 3/1996 | Gellert |
| 5,544,649 | A | 8/1996 | David et al. |
| 5,554,160 | A | 9/1996 | Caillouette |
| 5,556,401 | A | 9/1996 | Caillouette |

FOREIGN PATENT DOCUMENTS

WO 88/06077 * 8/1988 .................. 600/38

OTHER PUBLICATIONS

FUFME, Fuck U Fuck Me Product Info, 1999.*
Odzer, ANCHOR, “Cybersex An online sexual revolution”, Jul. 13, 1998 from www.ahref.com/guides/culture/199807/0713odzerprintable.html.
*Virtual Sex Machine*, www.vrinnovations.com,© 1998 Virtual Reality Innovations.

* cited by examiner

*Primary Examiner*—John P. Lacyk
(74) *Attorney, Agent, or Firm*—Blank Rome Comisky & McCauley LLP

(57) ABSTRACT

An interactive virtual sexual stimulation system has one or more user interfaces. Each user interface generally comprises a computer having an input device, video camera, and transmitter. The transmitter is used to interface the computer with one or more sexual stimulation devices, which are also located at the user interface. In accordance with the preferred embodiment, a person at a first user interface controls the stimulation device(s) located at a second user interface. The first and second user interfaces may be connected, for instance, through a web site on the Internet. In another embodiment, a person at a user interface may interact with a prerecorded video feed. The invention is implemented by software that is stored at the computer of the user interface, or at a web site accessed through the Internet.

40 Claims, 5 Drawing Sheets

METHOD AND DEVICE FOR INTERACTIVE VIRTUAL CONTROL OF SEXUAL AIDS USING DIGITAL COMPUTER NETWORKS

BACKGROUND OF THE INVENTION

1. Field of the Invention

The present invention relates to remotely-controlled sexual aids. More particularly, the invention relates to sexual aids that are controlled through personal computers and digital computer networks, such as the Internet, by user interactive programs.

2. Description of the Related Art

A number of sexual stimulation aids or devices are currently offered that are controlled by a person for self-stimulation, or to stimulate a third party (the "recipient"). For clarity, the term "operator" is used to refer to the person or persons operating the stimulation aid, and the term "recipient" is the person or persons being stimulated by the aid. It is to be understood that the operator and the recipient may be the same party or two different parties.

Stimulation devices have been developed that allow the operator to control the rate of stimulation, as well as other factors that affect the amount of stimulation imparted to the recipient. U.S. Pat. Nos. 5,501,650 and 4,790,296 to Gellert and Segal, respectively, show two different stimulation devices that permit the operator to control the amount of stimulation imparted to the recipient. In addition, U.S. Pat. No. 5,490,784 to Carmein shows a virtual reality system having a "virtual sex" application with an interactive solid that simulates a human partner.

These stimulation aids, however, require that the operator directly engage the stimulation aid. Only several stimulation aids are known that allow the stimulation aid to be operated by a remote controller-type device, such as shown in U.S. Pat. No. 4,834,115 to Stewart entitled "Penile Constrictor Ring," U.S. Pat. No. 4,412,535 to Teren entitled "Remotely Controlled Massaging Apparatus," U.S. Pat. Nos. 3,978,851 and 3,874,373, each to Sobel and entitled "Massaging Apparatus," and U.S. Pat. No. 5,454,840 to Krakovsky et al. entitled "Potency Package."

Nonetheless, these prior art devices all have the disadvantage that the operator must be in close proximity to the recipient. Medical communication systems are known that enable medical personnel located at a central station to monitor devices located at a patient via computer control over an existing telephone network. Medical communications systems are shown, for instance, by U.S. Pat. Nos. 5,462,051, 5,544,649 and 5,467,773 to Oka et al., David et al., and Bergelson et al., respectively. However, these medical communication systems are not readily suitable for use for sexual stimulation aids. Thus, no system enables an operator to control a stimulation aid from a location remote from the recipient.

SUMMARY OF THE INVENTION

Accordingly, it is a primary object of the invention to provide a system that permits an operator to have interactive control of a sexual aid used to stimulate a recipient that is remotely located from the operator. It is a further object of the invention to provide a system in which an operator may stimulate a recipient over currently existing computer networks, such as the Internet. It is yet another object of the invention to provide a multi-media event, such as a prerecorded video feed, that automatically operates a stimulation aid located at a user interface.

In accordance with these and other objectives, the present invention is a system having one or more user interfaces. Each user interface generally comprises a computer. The user interface may be connected to an input device, video camera, and/or signal interface. The signal interface is used to interface the computer with one or more sexual stimulation devices, which are also connected to the user interface. In accordance with the preferred embodiment, a person at a first user interface controls the stimulation device(s) located at a second user interface. The first and second user interfaces may be connected, for instance, through a web site on the Internet.

In another embodiment, a person at a user interface may interact with a multi-media event, such as a prerecorded video feed. The invention is implemented by software that is stored at the computer of the user interface, or at a web site accessed through the Internet.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
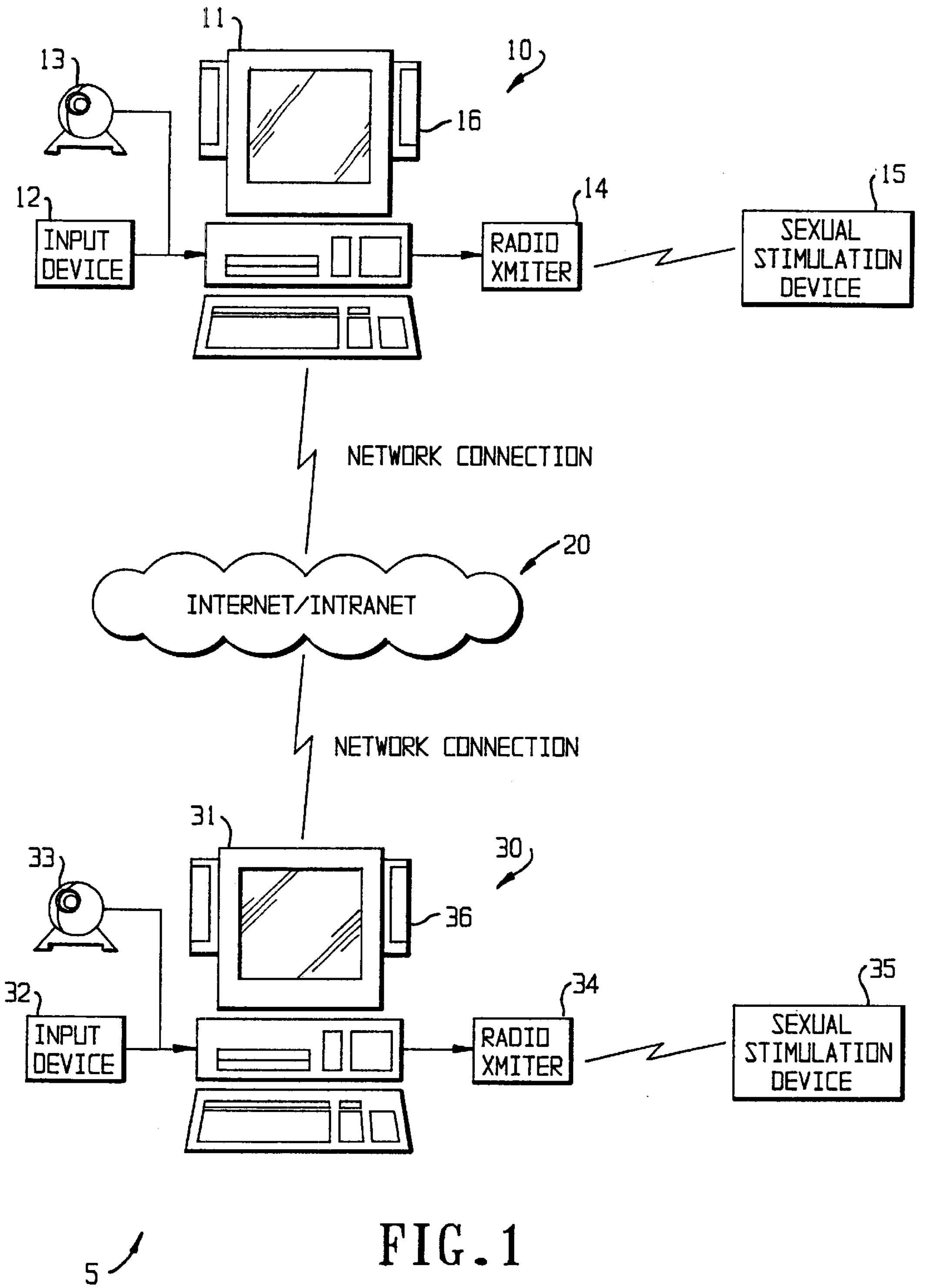
FIG. 1 is a diagram of the overall system for interactive use by two or more users in accordance with the preferred embodiment of the invention.

In describing preferred embodiments of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Turning to the drawings, FIG. 1 shows the overall system of the invention, generally designated by the numeral 5. The system 5 generally has a first user interface, generally designated by the numeral 10, connected through a network, generally designated by the numeral 20, to a second user interface, generally designated by the numeral 30. Each of the first and second user interfaces 10, 30 preferably comprise a personal computer 11, 31. Various devices are connected to the user interfaces 10, 30, including input devices 12, 32, video cameras 13, 33, signal interface or remote transmitters 14, 34, sexual stimulation devices 15, 35 and/or speakers 16, 36.

As used herein, the term "user" refers to a person or persons that is at any one of the user interfaces 10, 30. A "user" may also be either an operator, recipient, or both an operator and a recipient.

In accordance with the first embodiment of FIG. 1, the first and second user interfaces 10, 30 are each connected to a network 20 by a network connection. The network may be the Internet, or an Intranetwork such as a Local Area Network. However, the first and second interfaces 10, 30 may also be directly connected together, such as in a local connection or via a bulletin board service. Still yet, the first and second interfaces 10, 30 may be connected in any other suitable manner.

A first user, located at the first user interface 10, may input commands or control signals into the computer 11 via input device 12 or the computer keyboard. The input device 12 may be, for instance, a joystick, mouse and/or microphone. Still yet, the input device 12 may be a custom designed input mechanism, such as an input device having acceleration sensor and both tactile input and feedback systems. Control signals input at the first interface may be used to control one or both of the sexual stimulation devices 15, 35 located at the first user interface 10 and the second user interface 30, respectively.

Real-time video images may also be captured by camera 13 and displayed at the display device of the first user interface 10 and/or the second user interface 30. Likewise, audio signals may be received at the first user interface 10 by a microphone (not shown) and output through speakers 16 and/or 36.

Thus, in the preferred embodiment shown in FIG. 1, commands are input by the user at the first user interface 10. The commands or control signals are then transmitted to stimulation devices 15, 35 at either the first or second user interfaces 10, 30 through remote transmitters 14, 34 and network 20. The user may select one or more of the stimulation devices 15, 35 located at the first user interface 10, second user interface 35, or any other user interface (not shown). Control signals transmitted by the first user interface 10 to stimulation device 15 need not be transmitted through the network 20.

The recipient located at each user interface 10, 30 engages the associated stimulation aid 15, 35 as required for the type of stimulation device being used. The selected stimulation devices 15, 35 are then operated by the control signals to vary the speed, multi-axis motion, pressure and type of stimulation to be imparted to the recipient. Multiple stimulation devices 15, 35 may be located at each user interface 10, 30, and operated by one or more transmitters 14, 34 at each interface. Each recipient may be fitted with one or more stimulation aids 15, 35, and multiple recipients and/or operators may be located at each user interface 10, 30.

The remote transmitters 14, 34 are connected to an input/output port of the computer 11, 31, such as the parallel port. The remote transmitters 14, 34 remove the risk of current leakage and other detrimental electrical signals that otherwise might be generated or received by the computer 11, 31. The remote transmitters 14, 34 preferably are either radio or infrared links that isolate the associated stimulation devices 15, 35 from dangerous current. Alternatively, the stimulation device may be directly wired to the computer with a current protection circuit. The transmitter 14 functions as an interface between the stimulation device 15 and the computer 11.

The sexual stimulation devices 15, 35 generally provide three basic types of stimulation: vaginal, penile and anal. However, the stimulation devices 15, 35 may also be a body massage or similarly suitable device. The transmitter 14 may be configured to be used in combination with any standard stimulation device that receives signals, such as those shown in U.S. Pat. Nos. 4,834,115 and 4,412,535 to Stewart and Teren, respectively, the disclosures of which are hereby incorporated by reference.

Standard stimulation devices 15, 35 that are not capable of receiving remotely transmitted signals (i.e., hard-wired devices, such as shown in U.S. Pat. No. 3,978,851 to Sobel) may be adapted to be directly connected (or through an interface) to the computer to receive control signals.

Accordingly, an operator at the first user interface 10 may control the functions of a physical sexual stimulation device 35 over unlimited distance using a personal computer 11 and the Internet 20 in a virtual interactive method using existing input devices 12. At the same time, that same operator at the first user interface 10 may also be a recipient that receives interactive audio and visual stimulation at a stimulation device 15 located at the first user interface 10.

The Internet 20 further allows for operators and recipients to select each other from services, such as adult entertainment chat rooms, or through pay sites having adult live video feeds. Any number of persons may interconnect to form a session, each joining as either an operator, recipient, or an observer, or as both an operator and a recipient. The parties may also transmit messages over the Internet during the course of the session.

Figure 2:
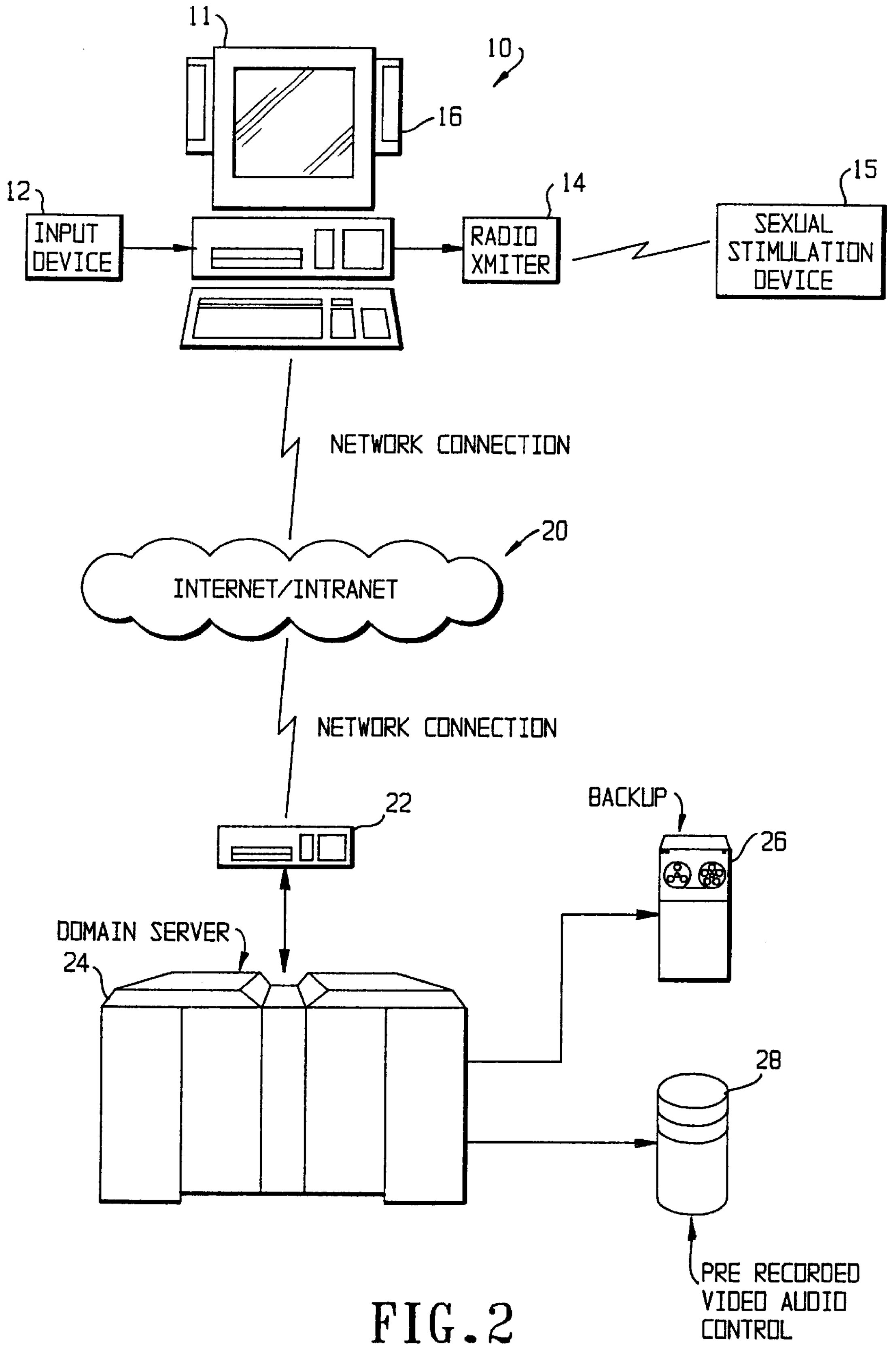
FIG. 2 is a diagram of the overall system for a user to interact with prerecorded video feeds in another embodiment of the invention.

Another embodiment of the invention is shown in FIG. 2 involving only a single user interface 10. The user interface 10 connects to a domain server 24 through the Internet 20 and router 22. The domain server controls a backup 26 and pre-recorded video and audio feeds stored at control unit 28.

According to this embodiment, a user located at the user interface 10 may access pre-recorded video and audio feeds at control unit 28. The user may, for instance, select from a variety of pre-recorded video feeds. The control unit 28 then plays the selected video feed. Control signals associated with the selected video feed can be transmitted to the stimulation device 15 during display of the video on the display device and over speakers 16.

As in the embodiment of FIG. 1, there may be multiple recipients and/or operators at the user interface 10. Likewise, each recipient may be fitted with one or more stimulation aids 15. A single transmitter 14 may control one or more stimulation aids 15, or multiple transmitters 14 may be provided. The user interface 10 may also include a video camera (not shown), so that the user may create a video feed for storage on the control unit 28.

Still yet, the embodiment of FIG. 2 may be combined with the embodiment of FIG. 1. Thus, users at multiple user interfaces 10, 30 may form a session to simultaneously view a single video feed. Video camera 13 and microphones (not shown) may also be used to add video and audio to the prerecorded video feed.

Figure 3:
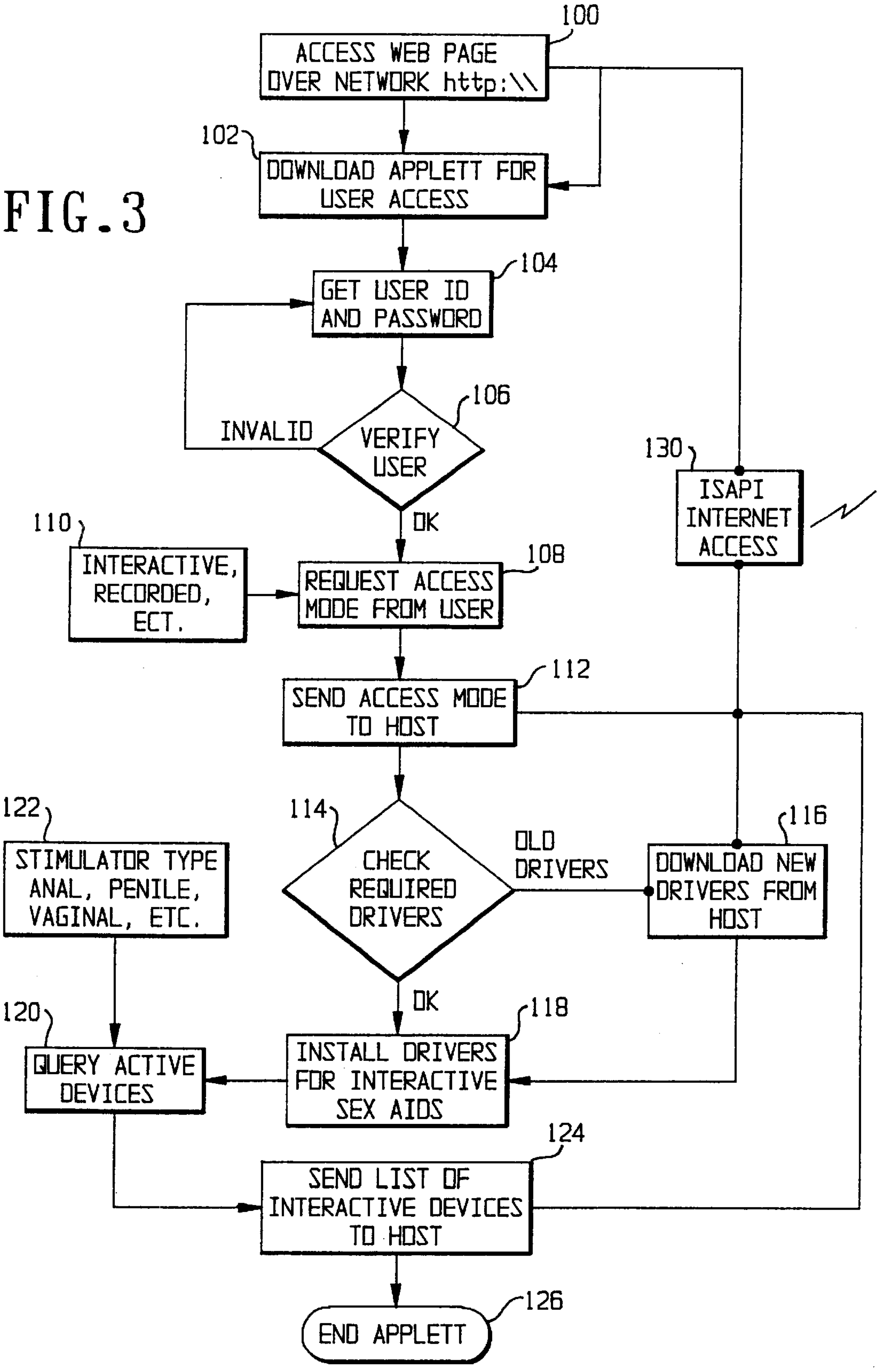
FIG. 3 is a flow chart for initiation of a user to log into a web site that implements the invention.

One possible implementation of the operation of the system will now be discussed starting with reference to FIG. 3. FIG. 3 shows network access by a user interface 10 to a web site controlled by server 24. Operation is preferably implemented by the use of a Java applet, though access may be achieved in any suitable manner. Starting with step 100, the user directs the computer 11 to access the desired web page over the Internet. This is typically done through the use of a standard Internet Service Application Program Interface (ISAPI) 130, such as WINDOWS® software In accordance with the preferred embodiment, the server 24 transmits an applet to the computer 11, step 102, which in accordance with the preferred embodiment prompts the user for an ID and password, step 104. If the password and ID are verified at step 106, the system proceeds to step 108. Otherwise, the user is returned to step 104.

Once the user has entered the correct ID and password, the user is then prompted to select the desired mode of operation, step 108. The preferred modes of operation are: two (or more) person interactive (FIG. 1) and one person pre-recorded (FIG. 2), block 110. The selected mode is then transmitted to the host, step 112, via the ISAPI 130.

The system then checks whether the computer 11 at the first user interface 10 has the required drivers, step 114. If the drivers stored on the computer 11 are old, the drivers are updated, step 116, and installed, step 118. If the drivers are current, step 114, the drivers are installed at step 118.

Following installation of the drivers, the active stimulation devices 15 are queried, step 120. Here, the possible active devices may be, for instance, anal, penile, vaginal, etc., as represented at block 122. The list of active devices are then sent to the host, step 124, and the applet ends, step 126. The query may also include a search of input devices 12, 13 that are connected to the computer 11.

Figure 4:
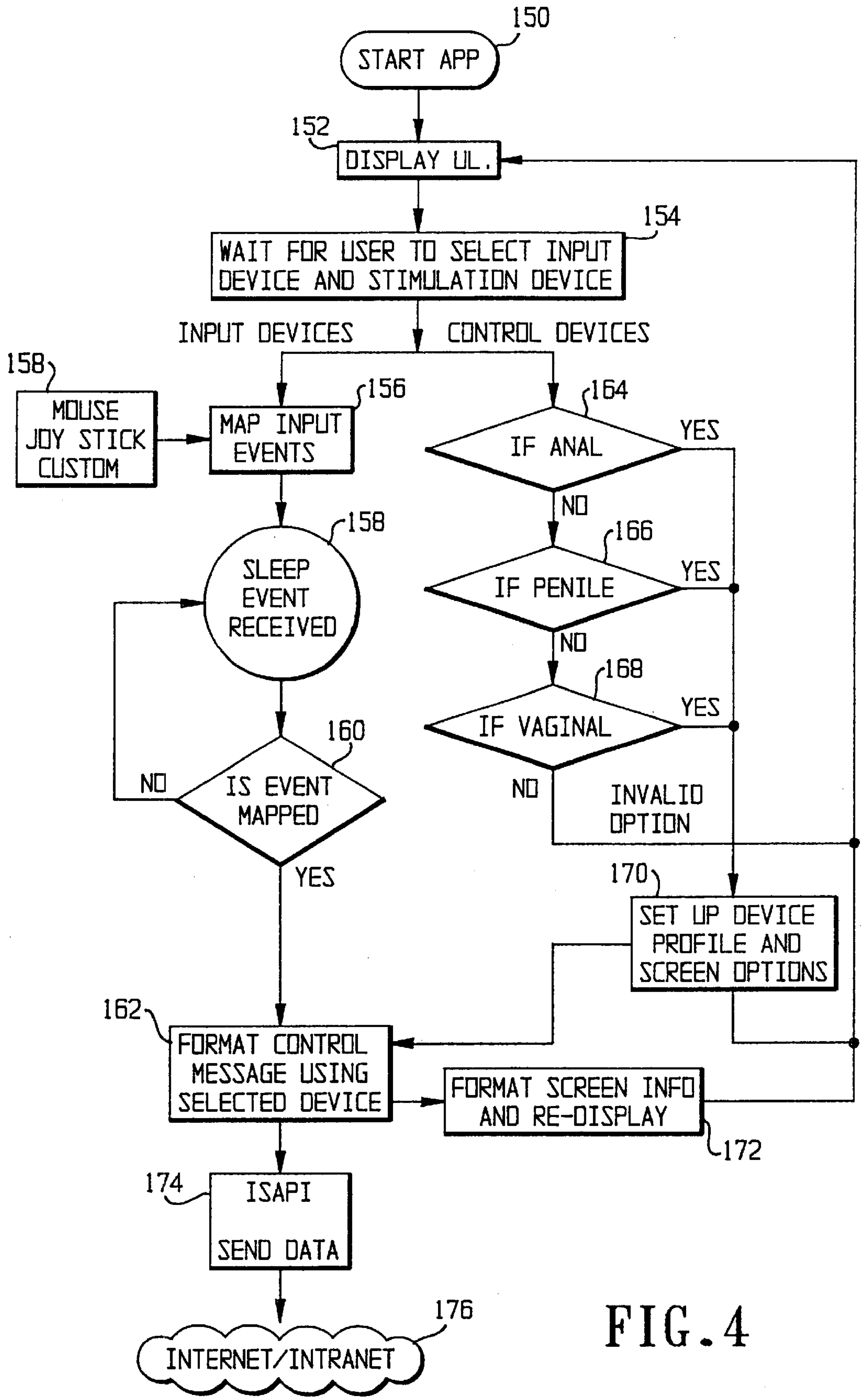
FIG. 4 is a flow chart for a user to select the types of input devices and stimulation aids that transmit control signals by an operator in accordance with the present invention.

Once the user interface 10 has accessed the network site, FIG. 3, the application will be executed in a frame window on a browser located at the user interface 10. Accordingly, the system picks up at FIG. 4, which formats the computer at the first user interface 10 to properly transmit control signals. FIG. 4 may be used, for instance, when a user at the first user interface 10 controls a stimulation aid 35 at a second user interface 30 (FIG. 1).

At step 150, the applet is started, and the user interface is displayed, step 152. The user interface is preferably a WINDOWS® interface. Menus and dialog selections for input devices 12 and stimulation aids 15 are displayed in a window. The list of input devices 12 and aids 15 is generated based upon the query of active devices, step 120. The user selects one or more stimulation aids 35 and input devices 12, 13 that are located at the first user interface 10, step 154.

In order for the computer 11 to properly format control messages generated by the user at the first user interface 10, the system must first know the type of input devices 12, 13 being used at the first user interface. This is performed along the left branch of FIG. 4. In addition, the computer 11 must also know the type of stimulation aid 35 that is to be controlled at the second user interface 30. This operation is performed along the right branch of FIG. 4.

The two branches meet at step 162, which combines the information regarding the input device being used by the user with the type of stimulation aid to be controlled. This information is then used to properly format control messages for transmission to the server or the second user interface 30.

The computer maps input events, step 156, based upon the type of input devices 12, 13 selected by the user, block 158. The system then enters a sleep mode until an event is received, step 158, from the selected input device. Once an event is received, step 158, the system checks whether the event is mapped, step 160. If the event is mapped, the system then proceeds to step 162 where it awaits the receipt of control messages from the user. If the received event is not mapped, the control received from the input device is not recognized, and the system returns to step 158.

In addition, the user selects the type of stimulation aid 35 that is to be controlled at the second user interface 10. The user simply selects which stimulation aid 35 is to be controlled from the list of aids sent by the host. Steps 164, 166, 168 determine, for instance, whether the type of stimulation aid 15 selected by the user is anal, penile or vaginal, respectively. If the device 15 is not recognized, the system returns to step 152. Otherwise, the device profile is set up and screen options are displayed to the user, step 170.

Once the input devices 12, 13 and stimulation devices 35 are selected, control signals generated by the user can then be properly formatted, step 162. The screen at the first user interface 10 is then updated, step 172, to display further instructions or options to the user. Information is transmitted, step 174, back over the Internet, block 176, to the server.

By way of example for illustrative purposes, one can envision that a user at the first user interface 10 is using a joy stick to control a stimulation aid located at the second user interface 30. An event might be the user moving the joy stick upwards, or pressing a button. If the stimulation aid is a massager, the movement of the joy stick upwards might generate a control signal to move the massager forward. If, on the other hand, the selected stimulation aid is a penile stimulator having a stroking mechanism, movement of the joy stick upwards may generate a control signal to increase the rate of the stroking mechanism. Accordingly, proper format of the control signal, step 162, depends upon the type of input device, as well as the stimulator being controlled.

Figure 5:
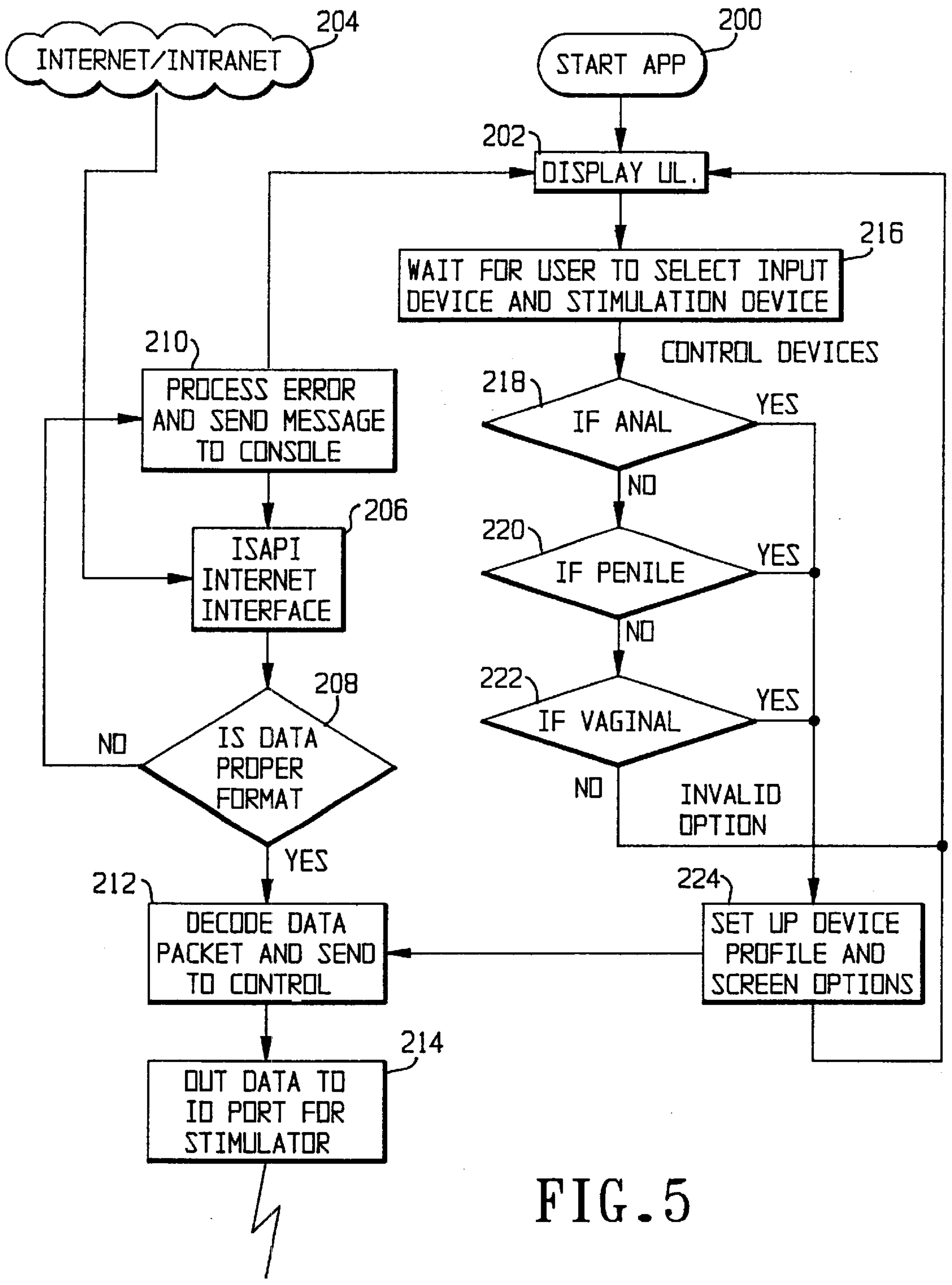
FIG. 5 is a flow chart showing operation of the system to decode control signals that are received and to format the control signals for transmission to the stimulation aid in accordance with the present invention.

FIG. 5 shows one implementation of the operation at the second (recipient) user interface, which is user interface 30 in the foregoing example. Thus, the operation of FIG. 5 details how control signals received from the first user interface 10 are processed. FIG. 5 also applies, for instance, to process control signals received from the server 24 when a one-person interactive prerecorded video feed is used, such as shown in FIG. 2.

Starting at step 200, an applet is initiated at the second user interface 30, the user interface is displayed, step 202, and the system awaits input by the user. Meanwhile, at blocks 204, 206, the user interface 30 receives a signal via the Internet. If the data is improperly formatted, step 208, an error signal is generated, step 210, and the system continues to await a valid message.

When properly formatted data is received, step 208, the data packet is decoded, step 212. However, in order for the data to be properly decoded and transmitted as a control signal to the stimulation aid 35, the computer 31 must know which stimulation device 35 is being used at the second user interface 30. The user may select the stimulation device and input device from amongst the active devices recognized, for instance, at step 120.

The data packet is decoded based upon the type of stimulation aid 35 that has been selected by the user, step 216. If the selected device is not anal, penile or vaginal, the computer indicates to the user that the user has selected an invalid option and returns to step 202. If, however, the selected aid 35 is recognized by the computer 31, steps 218, 220 and 222, the device profile is set up together with the screen options, step 224. The profiles are then used to decode the data packet, step 212. After the data packet has been decoded, it is sent through the Input/Output port of the computer to the transmitter 34 and respective stimulation device 35.

In addition to the steps of FIGS. 3–5, each computer 11, 31 at the various user interfaces may perform a query to determine which input devices and stimulation aids 15 are connected at that user interface. The user interfaces 10, 30 then communicate with each other (and/or to server 24) to indicate which stimulation aids and input devices are active or desired to be used. The control signals transmitted by the first user interface 10 (or server 24) to the second user interface 30 may then be properly formatted by the first user interface and decoded by the second user interface. The server may also operate to process and format messages between the first and second user interfaces 10, 30, based upon information received by computers 11, 31 indicating the types of input devices and stimulation aids located at the respective interfaces and desired to be used by the user.

In accordance with the preferred embodiment of the invention, the system and method of the present invention is implemented by computer software. The software may be stored on a CD-ROM at the user interface, or stored locally within a single free-standing computer or at a server for a group of computers networked together. The computer software may also be remotely located at a host server 24 that is accessed through a communication medium 20, such as the Internet.

In addition, the input devices 12, 13, as well as the stimulation device 15, may integrated into a single unit together with the user interface 10. Thus, for instance, a portable unit may be configured that includes an input device, stimulation aid, and offers a connection to the Internet for communication with other remote units.

The foregoing descriptions and drawings should be considered as illustrative only of the principles of the invention. The invention may be configured in a variety of shapes and sizes and is not limited by the dimensions of the preferred embodiment. Numerous applications of the present invention will readily occur to those skilled in the art. For example, prepackaged user interactive games may be distributed on digital medium for single user stimulation. In addition, the computer 11 may be any suitable interface, such as a television that communicates through the Internet or a processor designed to implement the invention. Therefore, it is not desired to limit the invention to the specific examples disclosed or the exact construction and operation shown and described. Rather, all suitable modifications and equivalents may be resorted to, falling within the scope of the invention.

What is claimed is:

1. A stimulation system comprising:

a display device;

a user interface connected to said display device, said user interface causing an image to be displayed on said display device and outputting a control signal; and, a stimulation device receiving the control signal from the user interface, said stimulation device imparting stimulation to the user in response to the control signal.

2. The stimulation system of claim 1, further comprising a signal interface connected to the user interface for receiving the control signal and transmitting the received control signal to said stimulation device.

3. The stimulation system of claim 2, wherein the signal interface comprises a radio transmitter.

4. The stimulation system of claim 2, wherein the signal interface comprises an infrared transmitter.

5. The stimulation system of claim 1, wherein the user interface comprises a computer.

6. The stimulation system of claim 1, the stimulation device comprising a sexual stimulation device, the control signal varying sexual stimulation imparted to the user.

7. The stimulation system of claim 1, wherein said display device, user interface and stimulation device are integrated into a single unit.

8. A stimulation system comprising:

a hand-operable input device for generating a command signal in response to an input received from a first user;

a first user interface connected to said input device, said first user interface generating a control signal based upon the command signal;

a second user interface remotely located from said first user interface, said second user interface receiving the control signal; and, a stimulation device receiving the control signal from said second user interface, said stimulation device imparting stimulation to a second user in response to the control signal.

9. The stimulation system of claim 8, further comprising a signal interface connected to said second user interface for receiving the control signal and transmitting the received control signal to said stimulation device.

10. The stimulation system of claim 9, wherein the signal interface comprises a radio transmitter.

11. The stimulation system of claim 9, wherein the signal interface comprises an infrared transmitter.

12. The stimulation system of claim 8, the first and second user interfaces each comprising a computer.

13. The stimulation system of claim 8, further comprising a video camera connected to said first user interface for recording images for display at said second user interface.

14. The stimulation system of claim 8, the stimulation device comprising a sexual stimulation device, the control signal varying sexual stimulation imparted to the second user.

15. The stimulation system of claim 8, the first and second user interfaces connected through a local area network.

16. The stimulation system of claim 8, the first and second user interfaces connected through a global network.

17. A stimulation system comprising:

a first hand-operable input device for generating a first command signal in response to an input received from a first user;

a first user interface connected to said first input device, said first user interface generating a first control signal based upon the first command signal and receiving a second control signal;

a first stimulation device receiving the second control signal from said first user interface, said first stimulation device imparting stimulation to the first user in response to receiving the second control signal;

a second input device for generating a second command signal in response to an input received from a second user;

a second user interface remotely located from said first user interface, said second user interface receiving the first control signal and generating the second control signal based upon the second command signal; and, a second stimulation device receiving the first control signal from said second user interface, said second stimulation device imparting stimulation to the second user in response to the first control signal.

18. The stimulation system of claim 17, further comprising a first signal interface connected to said first user interface for receiving the second control signal and transmitting the received second control signal to said first stimulation device.

19. The stimulation system of claim 18, further comprising a second signal interface connected to said second user interface for receiving the first control signal and transmitting the received first control signal to said second stimulation device.

20. The stimulation system of claim 17, the first and second user interfaces each comprising a computer.

21. The stimulation system of claim 17, further comprising a first video camera connected to said first user interface for capturing images for display at said second user interface.

22. The stimulation system of claim 17, the first and second stimulation devices each comprising a sexual stimulation device, the first and second control signals varying sexual stimulation imparted to the first and second users, respectively.

23. The stimulation system of claim 17, wherein the first and second control signals occur substantially simultaneously.

24. The stimulation system of claim 17, the first and second user interfaces connected through a global network.

25. A stimulation system comprising a user interface outputting an automated control signal including an image, a stimulation device receiving the automated control signal from the user interface, and a display device connected to said user interface and displaying the image, wherein said stimulation device imparts stimulation to a user in response to the automated control signal.

26. The stimulation system of claim 25, wherein the automated control signal is based upon prerecorded information.

27. The stimulation system of claim 26, wherein the prerecorded information is stored at said user interface.

28. The stimulation system of claim 26, wherein the prerecorded information is stored at a server accessed by said user interface through a global network.

29. The stimulation system of claim 25, further comprising a server located remotely from said user interface, said server generating the automated control signal and transmitting the automated control signal to said user interface.

30. The stimulation system of claim 25, further comprising a remote user interface, said remote user interface generating the automated control signal and transmitting the automated control signal to said user interface.

31. The stimulation system of claim 1, wherein said user interface receives an image signal having the image.

32. The stimulation system of claim 31, wherein the control signal causes said stimulation device to impart stimulation to the user based upon the image of the image signal.

33. The stimulation system of claim 1, wherein the image is a video image.

34. The stimulation system of claim 1, wherein the image is a real-time image.

35. The stimulation system of claim 1, wherein said user interface is connected to a global network, and the image signal is received from the global network.

36. The stimulation system of claim 8, wherein said hand-operable input device comprises either a mouse or a joystick.

37. The stimulation system of claim 25, the user interface outputting one of a plurality of user selectable automated control signals.

38. A stimulation system comprising:

an input device for generating a command signal in response to an input received from a user;

a computer connected to said input device, said computer generating a control signal based upon the command signal; and, a stimulation device receiving the control signal from the computer, said stimulation device imparting stimulation to the user in response to the control signal.

39. A stimulation system comprising:

an input device for generating a command signal in response to an input received from a first user;

a first user interface connected to said input device, said first user interface generating a control signal based upon the command signal;

a camera connected to said first user interface for recording images;

a second user interface remotely located from said first user interface, said second user interface receiving the control signal and the recorded images;

a stimulation device receiving the control signal from said second user interface, said stimulation device imparting stimulation to a second user in response to the control signal; and, a display device connected to said second user interface for displaying the recorded images.

40. A stimulation system comprising a server generated a control signal, a user interface remotely located from said server and receiving the control signal, and a stimulation device receiving the control signal from the user interface, said stimulation device imparting stimulation to a user in response to the control signal.

* * * * *